(12) United States Patent
Tepper et al.

(10) Patent No.: US 7,549,598 B2
(45) Date of Patent: Jun. 23, 2009

(54) METHOD OF MAKING AND APPLYING VOLATILE SUBSTANCE-CONTROLLING COMPOSITION

(75) Inventors: Bruce Ernest Tepper, Cincinnati, OH (US); Ravindra Ranatunga, West Chester, OH (US); Victor Nicholas Vega, Cincinnati, OH (US); Ramon Andres Urteaga, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 262 days.

(21) Appl. No.: 11/803,603

(22) Filed: May 15, 2007

(65) Prior Publication Data

US 2007/0224078 A1  Sep. 27, 2007

Related U.S. Application Data

(62) Division of application No. 10/699,470, filed on Oct. 31, 2003, now Pat. No. 7,234,648.

(51) Int. Cl.
*B05D 7/22* (2006.01)
*A61L 9/04* (2006.01)

(52) U.S. Cl. .............................. 239/53; 239/6; 239/56; 264/4.1; 427/230; 427/238; 510/441

(58) Field of Classification Search ............ 239/6, 239/53, 55, 56; 364/4.1; 427/230, 238; 510/441
See application file for complete search history.

(56) References Cited

U.S. PATENT DOCUMENTS 4,614,299 A  *  9/1986  Van Loveren et al. .......... 239/6

| | | |
|---|---|---|
| 5,554,143 A | 9/1996 | Roe et al. |
| 5,554,144 A | 9/1996 | Roe et al. |
| 5,554,145 A | 9/1996 | Roe et al. |
| 5,555,142 A | 9/1996 | Komai et al. |
| 5,556,394 A | 9/1996 | Roe et al. |
| 5,558,661 A | 9/1996 | Roe et al. |
| 5,575,784 A | 11/1996 | Ames Ooten et al. |
| 5,607,760 A | 3/1997 | Roe |
| 5,609,587 A | 3/1997 | Roe |
| 5,624,426 A | 4/1997 | Roe et al. |
| 5,643,588 A | 7/1997 | Roe et al. |
| 5,906,603 A | 5/1999 | Roe et al. |
| 5,957,906 A | 9/1999 | Roe et al. |
| 5,968,025 A | 10/1999 | Roe et al. |
| 5,997,521 A | 12/1999 | Robles et al. |
| 6,107,537 A | 8/2000 | Elder et al. |
| 6,118,041 A | 9/2000 | Roe et al. |
| 7,234,648 B2 | 6/2007 | Tepper et al. |

FOREIGN PATENT DOCUMENTS

| | | | |
|---|---|---|---|
| EP | 0 347 746 | * | 12/1992 |
| JP | 59-044308 | * | 3/1984 |
| JP | 60-018171 | * | 1/1985 |
| WO | WO 00/04938 | * | 2/2000 |

* cited by examiner

*Primary Examiner*—H. (Holly) T Le
(74) *Attorney, Agent, or Firm*—John P. Colbert

(57) ABSTRACT

A method of controlling the spread of volatile substances is provided. The method comprises the steps of: a) impregnating a fragrance component comprising at least one PRM onto a plurality of surfaces of a sorbent to form a volatile substance-controlling composition; and b) disposing the volatile substance-controlling composition into an article wherein the fragrance component is released from the sorbent primarily in the presence of one or more volatile substances when the volatile substances are adsorbed by the sorbent.

8 Claims, No Drawings

METHOD OF MAKING AND APPLYING VOLATILE SUBSTANCE-CONTROLLING COMPOSITION

CROSS REFERENCE TO RELATED APPLICATION

This application is a divisional of U.S. application Ser. No. 10/699,470, filed Oct. 31, 2003 now U.S. Pat. No 7,234,648, the substance of which is incorporated herein by reference.

FIELD OF THE INVENTION

The present invention relates to volatile substance-controlling compositions, a method of producing these compositions, articles of manufacture comprising these compositions, and/or their method of use, wherein the volatile substance-controlling composition comprises a sorbent with surfaces and a fragrance component impregnated onto the surfaces of the sorbent where the fragrance component is released primarily in the presence of a volatile substance and not substantially released in the absence of a volatile substance. These dual-purpose compositions involve volatile substance sorption directly linked to fragrance release without need for other intervening (or activating) factors.

These compositions are designed to control volatile substances, particularly malodors, caused by a broad spectrum of organic odiferous materials, such as those associated malodors resulting from bodily fluids and feces, putrefying organic wastes, combustion by-products, and the like, any of which may or may not contain reactive functional groups. This invention is further designed to remain shelf-stable for a substantial period of time with minimal or no loss of fragrance. The present invention is intended for use in a broad range of applications wherein malodors are controlled in a responsive and proportional manner, i.e., sorption of malodor directly and proportionally causes the release of fragrance.

BACKGROUND OF THE INVENTION

It has long been known that odors from various sources are difficult to control, including malodors associated with bodily fluids, feces, putrefying organic wastes, combustion by-products, and the like. Two common strategies of malodor control are sorption and fragrance masking. When used individually and/or in combination these strategies often provide limited and/or unsatisfactory odor control for obnoxious odors like those associated with feces, stale urine, menses, vomitus, tobacco smoke, fish, putrefying food wastes, and the like.

The most common reason for failure of a pure sorption strategy to control malodors is that, in the absence of 100% sorption of malodors, many residual non-sorbed malodors at parts per billion (ppb) levels or lower are perceived as obnoxious by humans. Near 100% sorption of malodors, which can be insufficient for success, is not easily attained in practice, but is sometimes approachable with a very high degree of malodor containment and/or the use of excess sorbent.

The most common reason for failure of a pure fragrance masking strategy to control obnoxious odors is that the amount of fragrance sufficient to mask the malodors is often just as obnoxious to those concerned with the problem as the malodors themselves. In addition, delivery of sufficient fragrance to mask strong malodors is difficult to achieve for any extended period of time due to rapid dispersion of the fragrance. Moreover, a method for as-needed, automated delivery of appropriate levels of masking fragrance has not existed in the past; hence, human intervention for delivery is needed.

Other reasons for failure common to both the sorption and fragrance masking strategies are a) the variety of individual malodor components from any given source and b) the variable presence of the various individual malodor components during any given malodor event. For example, while activated carbon has long been known to excel at sorbing a wide variety of malodors, no single sorbent is capable of sorbing all of the various malodor components that can be associated with many sources of strong malodors, such as feces, menses, vomitus, putrefying organic waste, and the like. Activated carbon, even when dosed with an adjuvant material such as citric acid or copper, is a relatively modest sorbent for ammonia, hydrogen sulfide, methyl mercaptan and other malodors from such sources. In addition, for any of the strong malodor sources the specific malodors will vary among sources and/or over time within sources. A mixture of various sorbents could, in theory, provide sorption capacity for all possible malodors, but oftentimes much of the sorbent mixture would be unnecessary or wasted when contained in durable articles or disposable articles. In the case of fragrance, it is difficult—perhaps impossible—to formulate any one fragrance composition capable of masking successfully so many different possible combinations of malodors.

The use of a combination of sorption and fragrance masking to achieve odor control has been proposed in the past, but has not been commercially adapted nor readily achieved for several reasons. Some relevant art teaches that use of a fragrance to mask malodor in absorbent articles may detract from the functionality of the malodor sorbent, presumably from the fragrance occupying sorption sites on the sorbent needed for malodor sorption, but no specific methods nor criteria are provided to overcome this problem. Other publications teach placing the malodor sorbent and the fragrance release source on opposite sides of a forced-air circulation system such that the malodors are sorbed prior to the deodorized air being distributed back to the room with fragrance; however, in practice, fragrance is eventually returned to the forced-air unit to be sorbed thereby substantially reducing fragrance delivery. None of these published odor control solutions adequately overcome problems of linking fragrance release to the malodor occurrence and concurrently controlling losses of fragrance from the odor composition when fragrance masking is unnecessary.

For moisture-activated compositions many sources of malodor such as feces, menses and combustion by-products have insufficient moisture to activate adequate fragrance release, and/or the initial presence of sufficient moisture does not coincide with the bulk of the malodor release, and/or the amount of fragrance release is insufficient to mask strong malodors. Moreover, previously published data demonstrate that fragrances are poorly retained by a sorbent carrier in the absence of a protective device or encapsulation such that fragrance is released continuously irrespective of the presence of malodors. At best what is claimed for such inventions is durable fragrance release. In contrast, the rate of fragrance release from a chemical bond can be better controlled. But, fragrance release is too slow compared to the rate of malodor dispersion. Finally, when thermal energy is used to release fragrance, the fragrance delivery system does not work or tends to work poorly under ambient conditions, i.e., in the absence of heat.

In summary, all of the previously proposed solutions lack direct linkage of fragrance release to the malodor source, i.e., none use malodors to directly trigger fragrance release or to provide fragrance release proportional to the malodors to be controlled.

Accordingly, the present invention overcomes the problems associated with controlling malodors by a combination of sorption and fragrance masking in an efficient and effective manner for a wide variety of applications. The present invention is useful for consumer products and other applications intended to control a variety of malodors, such as from bodily fluids, putrefying organic wastes, combustion by-products, and the like, in a cost-effective manner using shelf-stable articles that minimize unnecessary, untimely, and/or excessive fragrance masking.

SUMMARY OF THE INVENTION

The present invention relates to a volatile substance-controlling composition comprising:
 a) a sorbent having a plurality of surfaces; and
 b) a fragrance component comprising at least one PRM, wherein said fragrance component is impregnated onto said surfaces of said sorbent and wherein in the presence of one or more volatile substances said fragrance component is released from said sorbent and said volatile substances are adsorbed by said sorbent. Additionally, the invention relates to methods of making the composition as well as articles that incorporate such a composition.

The present invention is, therefore, a dual-purpose volatile substance controlling composition involving volatile substance sorption directly linked to fragrance release without need for other intervening (or activating) factors, and is designed to control volatile substances caused by a broad spectrum of odoriferous organic materials, such as those associated with bodily fluids and feces, putrefying organic wastes, combustion by-products, and the like, which may or may not contain reactive functional groups. This invention is further designed to remain shelf-stable for a substantial period of time with minimal or no loss of fragrance.

The present invention is intended for use in a broad range of applications wherein malodors are controlled in a responsive and proportional manner, i.e., sorption of malodor directly and proportionally causes the release of masking fragrance.

DETAILED DESCRIPTION OF THE INVENTION

As used herein "absorbent" means a liquid and/or solid material into which are taken in one or more other gaseous, liquid and/or solid materials.

As used herein "adsorbent" means a liquid and/or solid material onto which a thin layer of one or more other gaseous, liquid and/or solid materials become adhered.

As used herein "sorbent" means an absorbent material and/or an adsorbent material.

As used herein "perfume raw material" or "PRM" means any individual organic or inorganic chemical compound that when in a gaseous state can potentially be perceived by the human olfactory sense.

As used herein "fragrance" means any mixture or composition consisting of one or more perfume raw material(s) with or without one or more carrier solvent(s).

As used herein "impregnate" means to bring in contact a gaseous, liquid or solid material, e.g., a fragrance or PRM component, and a second solid material, e.g., a sorbent, to form an association of the first material with the second material, wherein unless otherwise specified the first material does not necessarily remain associated with or retained by the second material at ambient environmental conditions in the absence of a mechanism or process of manufacture to retard dissociation of the first material from the second material.

As used herein "gas displacement" means the phenomenon in which one gaseous material causes a second non-gaseous material that is associated with a substrate, e.g., a sorbent, to become dissociated from a physical site of the substrate, e.g., on a surface of an adsorbent, and wherein the first material changes to a non-gaseous state and becomes associated with the substrate.

As used herein "fragrance masking" or "masking" means to hide or disguise the olfactory perception of one or more volatile substances with a fragrance or PRM wherein there is no implication of interaction specifically between the volatile substance(s) and the fragrance or PRM.

As used herein "ambient environment" is meant the commonplace temperature in which the invention is used; e.g., for room deodorization at 18 to 30° C. and 40 to 60% relative humidity (RH) common to enclosed spaces in which humans typically inhabit, work, visit and/or transit in developed countries.

Sorbent

The volatile substance controlling-composition of the present invention includes a sorbent that is useful for sorbing volatile substances to its surfaces. The sorbent has a plurality of surfaces onto which substances may adhere. Preferably, the sorbent is a material selected from the group consisting of activated carbon, activated alumina, amorphous or crystalline silica, zeolite, ion exchange resin, metal bicarbonate, carbonate, cyclodextrin, metal oxide, crosslinked polyacrylate, and combinations thereof. More preferably, however, the sorbent is activated carbon.

The intended application of the composition of the present invention determines the form of the sorbent to use. Suitable forms of sorbent, particularly activated carbon, including powders, soot, granules, fibers and/or cloth. There are at least five general classes of application for use of the compositions: 1) direct use such as powder form for carpet deodorization, cat litter, vomitus deodorizer, etc., 2) in a cartridge or canister, e.g., as filter media, 3) incorporated into or onto substrates like paper, non-wovens, air-laid fibers, porous and non-porous films, and the like, e.g., as materials incorporated into absorbent articles, or as filters, dust mitts and dryer sheets, 4) fibrous wovens or cloths, and 5) in formulations, e.g., as an ingredient for toothpaste or chewing gum.

Each class of application has preferred forms of sorbent. Using activated carbon as an example, for direct use the preferred form is granules ranging in diameter size from about 40 µm to about 2,000 µm diameter, more preferably, from about 80 µm to about 1,000 µm diameter, and most preferably from about 125 µm to about 500 µm diameter. For cartridges, the preferred form is that of fibers and/or cloth, preferably from about 100 µm to about 5,000 µm thick, more preferably, from about 200 µm to about 2,500 µm thick, and most preferably from about 700 µm to about 1,400 µm thick. For canisters, the preferred form is granular wherein the granules range in diameter size from about 40 µm to about 10,000 µm diameter, more preferably, from about 125 µm to about 5,000 µm diameter, and most preferably from about 500 µm to about 2,500 µm diameter. For incorporation into substrates, the preferred form is also granular wherein the granules range in diameter size from about 40 µm to about 10,000 µm diameter, more preferably, from about 80 µm to about 2,500 µm diameter, and most preferably from about 125 µm to about 1,200 µm diameter. For incorporation onto substrates, the preferred form is granular as well wherein the granules range in diameter size from about 10 µm to about 1,000 µm diameter, more preferably, from about 35 µm to about 500 µm diameter, and most preferably from about 45 µm to about 180 µm diameter. For formulations, the preferred form is granular wherein the granules range in diameter size from about 1 µm to about 1,000 µm diameter, more preferably, from about 20 µm to about 210 µm diameter, and most preferably from about 35 µm to about 125 µm diameter.

Examples of activated carbon granules that are suitable for inclusion in the compositions of the present invention include, but are not limited to, coal-based Filtersorb 600 (CCC F600) 40×80 mesh size from Calgon Carbon Corporation (CCC) of Pittsburgh, Pa., USA, wood-based RGC 80×325 mesh size from Westvaco Corporation of Charleston, S.C., USA, and coconut shell-based 95% 325 mesh activated carbon from Jacobi Carbons Limited of Merseyside, UK.

When activated carbon is the sole sorbent used in the compositions of the present invention, it is present preferably in an amount from about 10 to 99 wt %, more preferably from about 50 to 95 wt %, and most preferably from about 70 to 90 wt %, by weight of the composition.

The volatile substance-controlling composition may be used in combination with one or more secondary sorbents which may include materials like those suitable for the first sorbent. For instance, a sorbent like activated carbon may have coated upon its surface one or more of the secondary sorbents, such as amorphous or crystalline silica, activated alumina, or zeolite. Alternatively, the activated carbon may be coated upon the surface of one or more of the secondary sorbents. Preferably, the composition comprises from about 1 to 99%, by weight of the total sorbent content, of the first sorbent. In preferred embodiments, the first sorbent is present in an amount of between 10 and 95% by weight, and most preferably between 40 and 90% by weight of the total sorbent, in the composition. Additionally, it is preferred that activated carbon is the first sorbent.

Fragrance Component

The compositions of the present invention additionally comprise a fragrance component that further comprises at least one perfume raw material (PRM). Applicants have found that the presence of such a fragrance component is required on the surfaces of the sorbent in order that it may be displaced by the volatile substances that occur upon use of the compositions of the present invention. It is desirable that at least a portion of the fragrance component is released in the presence of the volatile substances at levels at least one thousand times higher than in their absence under ambient conditions. Preferably, the compositions comprise from about one to about twelve perfume raw materials, more preferably about two to about six PRMs, and most preferably about three to about four PRMs. In preferred embodiments the perfume raw materials are selected from the group consisting of linear aliphatic, branched aliphatic, aromatic, polyaromatic, and/or heterocyclic organic compounds having at least one of the following functional groups: carboxylic acid, alcohol, aldehyde, amine, chylene, ester or ketone. More preferably, the PRMs of the present invention may be selected from the group consisting of phenylethyl acetate, ethyl acetate, ethyl butyrate, benzyl acetate, butyl butyrate, butyl acetate, carvone, cinnamaldehyde, citronellal furfural, 2-hexenal, a-ionone, lauraldehyde, d-limonene, linalool, b-myrcene, pheylethyl alcohol, a-pinene, propyl formate, valerolactone, isobomyl acetate, p-anisaldehyde, and combinations thereof. Even more preferably, the PRMs are selected from the group consisting of phenylethyl acetate, benzyl acetate, butyl butyrate, carvone, citronellal furfural, 2-hexenal, a-ionone, lauraldehyde, d-limonene, linalool, b-myrcene, pheylethyl alcohol, a-pinene, valerolactone, acetone, ethanol, isobomyl acetate, and cormbinations thereof. Most preferably, the PRMs are selected from the group consisting of furfural, 2-hexenal, d-limonene, b-myrcene, a-pinene, valerolactone, isobomyl acetate, and combinations thereof.

Without being limited by theory, Applicants believe when loaded onto the surfaces of the sorbent at a level of least about 10% of the composition, the PRMs of the fragrance component reduce the sorption capacity of the sorbent for specific malodors by less than about 10%, preferably by less than about 5%, and most preferably by less than about 2.5%. In other words, impregnation of PRMs onto the sorbent does not impede its ability to adsorb malodors. Moreover, the fragrance component of the volatile substance-controlling composition is capable of substantially masking any unsorbed residual malodors present without producing an overbearing or excessive level of fragrance.

Moreover, Applicants have found that the constitution of compositions of the present invention tends to depend on the type of volatile substances that need to be managed in the environment. That is, the type of volatile substances that need to be sorbed to the surfaces of the sorbent determine which PRMs are impregnated onto the surfaces of the sorbent since certain PRMs will only be displaced in the presence of certain volatiles. An overriding factor that determines the type of PRMs to be utilized in the compositions is the "use" condition for the composition. For instance, if the compositions are incorporated into a diaper, it is clear that only certain PRMs are necessary and operable for the function of adsorbing the malodors associated with feces and urine. Likewise, in the event the compositions are intended for use in a water filtration unit, it may be necessary that the compositions remain stable in aqueous environments as well as those that are adaptable to temperature change. Additional uses for these compositions include dusting mitts, cleansing pads, clothes dryer aids, filters, diapers, incontinence products, sanitary napkins, feminine care products, hazardous material regimens, etc. Therefore, the use will drive the "use" conditions, i.e., suitable temperature range for release of the fragrance component and sorption of the volatile substance at issue. For example, common absorption articles like diapers, training pants, incontinence articles and the like that are worn require that the invention work primarily between 30 and 40° C. and be completely stable—no substantive loss of impregnated fragrance—below 30° C. The invention when placed in dust mitts, passive or active room deodorizers, or as filters for forced air cooling or heating systems should work primarily between 18 and 30° C.

A preferred embodiment of the present invention includes the use of the compositions in the context of an absorbent article. Suitable absorbent articles include diapers, feminine care products such as sanitary napkins, pantiliners, and other disposable products like incontinence articles, training pants, and related products. Typically, such absorbent articles include a substrate component that is selected from the group consisting of topsheets, backsheets, absorbent cores, waistbands, leg cuffs, side panels, and combinations thereof. According to the present invention, the volatile substance controlling compositions may be disposed adjacent to any one or more of these substrate components.

Method of Use

The present invention additionally relates to utilizing the disclosed compositions to control the spread of volatile substances. Such a method comprises the steps of: a) impregnating a fragrance component onto a plurality of surfaces of a sorbent to form a volatile substance-controlling composition;

and b) disposing the volatile substance-controlling composition into an article wherein the fragrance component is released in the presence of volatile substances common to feces, bodily fluids, decaying food wastes or combustion gases of organic materials and wherein the volatile substances are adsorbed onto the surfaces of said sorbent. Moreover, those parameters that are preferred relative to the compositions of the present invention are equally applicable in the instance of this method of use.

Method of Making

The volatile substance-controlling compositions of the present invention, which may be granular or even fibrous in nature, are produced by introducing the liquid and/or gaseous fragrance component under pressure into a sealed mixing vessel in which the sorbent is being continuously mixed. The fragrance component is added to the sorbent preferably in an amount from about 1 to about 90 wt %, more preferably from about 5 to about 50 wt %, and most preferably from about 10 to about 30 wt %, by weight of the composition. The fragrance component is added to the sorbent via dissolution of the component in a solvent, which is preferably a solvent with a low boiling point and not adsorbed well on activated carbon.

Another preferred embodiment of the volatile substance-controlling composition is a sorbent impregnated with fragrance that is further contained within an air-permeable "chamber". The chamber may be comprised of paper, paperboard, wood, woven materials including cotton and polyester, nonwoven materials including films and laminates, ceramics including clays and porcelain, glass, metals including aluminum, steel, tin and bronze, or any combination thereof, wherein the chamber materials may or may not be coated to provide a moisture barrier to the contents. The chamber is a housing for the invention in various applications, such as a passive or active control article for interior living spaces or transportation vehicles.

Another preferred embodiment of the volatile substance-controlling composition includes a sorbent impregnated with fragrance wherein the composition is placed between film, nonwoven or laminate materials, wherein the film, nonwoven or laminate may be incorporated into an article. Films can be single or multiple (e.g., co-extruded) layers of cast or blown type. Nonwovens can be spunbonded, carded, airlaid by calendar or air-through bonded, needle punched, melt blown, or spun laced. Laminates can be any combination of nonwovens and cast films joined by direct extrusion coating, adhesive, thermal bonding, pressure bonding, or ultrasonic bonding. Laminates can also be any combination of two or more nonwovens joined by adhesive, thermal bonding, pressure bonding, or ultrasonic bonding.

Further embodiments of the volatile substance-controlling composition encompass active and passive volatile substance control systems, wherein "active" systems have integrated powered air circulation and "passive" systems rely on ambient air circulation which may or may not have powered air circulation from an independent source. Examples of active systems include those involving an independent forced-air system to clean, heat and/or cool, humidify or dehumidify the interior space of a building, a room, or a surface transport or an air transport vehicle, or to manage odors in a diaper pail or garbage can, or any of the preceding wherein the volatile substance-controlling composition is a filter used in conjunction with forced-air devices. Examples of passive systems comprising the volatile substance-controlling composition include containers into which are placed malodorous materials for storage, transport and/or disposal; chambers, sheets or other formats of the volatile substance-controlling composition that are placed into the interior space of a container, refrigerator, portable toilet, room or building, surface transport or air transport vehicle; and an absorbent article such as a diaper, sanitary napkin, pantiliner, incontinence pad, underarm shield, bandage and/or wound dressing, and the like.

Additional suitable articles of the present invention include those which are non-absorbent, such as an air filter or portion of an air-filtering device as might be found on an electrostatic precipitator, air conditioning and/or heating unit for a living space or transport vehicle, or other devices in which an air cleaning filter might be included such as a vacuum cleaner, refrigerator, "smoke-less" ashtray, pet litter box, and the like.

EXAMPLES

The present volatile substance-controlling compositions can be produced using a variety of equipment types and ranges of process parameters like mixing speeds, mixing and dosing durations, temperature, pressure etc. The specific process used to manufacture the compositions of the present invention depends upon the nature of the PRMs being impregnated into the sorbent. Some examples of preferred processes are illustrated below.

Example 1

A composition according to the present invention is made as follows. Activated carbon granule 800 g CCC F600 from Calgon Carbon Corporation, Pittsburgh, Pa., U.S.A. of nominal 40 mesh size is loaded into a sealable mixing chamber of a Tilt A Plow Mixer, Model 4HN from Processall Inc., Cincinnati, Ohio, U.S.A. The Tilt-A-Plow mixing chamber has a water-cooling mixing jacket set to 21° C. (70° F.) and contains two mixing mechanisms: a mixer/plow that is set to run at 250 rpm and a mill/chopper set to run at 2000 rpm. Separately, 200 g of fragrance butyl butyrate from Sigma-Aldrich, St. Louis, Mo., U.S.A. was loaded into a pressure pot (dosing canister) certified up to 140 psi from Alloy Products Corporation (Waukesha, Wis.) and the contents are pressurized to 80 psi. The fragrance is dosed into the mixing chamber from the pressure pot through a one-way valve fitted to an inlet port of the mixing chamber between 15 and 75 seconds of a 300 second mixing cycle. The mixing chamber is slowly vented at the end of the mixing cycle and the finished product removed into sealable containers.

Example 2

A composition of the present invention is made as detailed above in Example 1 with the exception that a sorbent is impregnated with fragrance using a continuous Shugi FX-100, manufactured by Hosokawa Bepex.

Example 3

Another composition according to the present invention is made as detailed in Example 1 except that 800 g RGC activated carbon granule 80×325 mesh size from Westvaco Corporation of Charleston, S.C. U.S.A. with 200 g of fragrance ethyl butyrate from Sigma-Aldrich, St. Louis, Mo., U.S.A.

Example 4

Another modification of the same process as for Example 1 impregnates 600 g RGC activated carbon granule 80×325 mesh size from Westvaco Corporation of Charleston, S.C. U.S.A. with fragrance in a two-step process. In the first step, fragrance A, 200 g of ethyl-butyrate from Sigma-Aldrich, St. Louis, Mo., U.S.A. is impregnated into the activated carbon during an initial 300 second mixing cycle as above. Excess ethyl butyrate may or may not be vented from the mixing chamber after the first mixing cycle. In the second step, fragrance B, 200 g of linalyl acetate from Sigma-Aldrich, St. Louis, Mo., U.S.A. is impregnated into the activated carbon during a second 300 second mixing cycle. The objective of the two step cycle is to impregnate the more volatile fragrance A first and displace a portion of it that resides closest to the surface of the activated carbon with fragrance B that is better retained on the activated carbon and blocks the premature release of A fragrance from adsorption sites further from the surface of the activated carbon.

Example 5

A sorbent (e.g., activated carbon in granular form such as those in Examples 1 through 4, or cloth form such as FM4/250 from Calgon Carbon Corporation, Pittsburgh, Pa., U.S.A.) and a small beaker containing an excess of a fragrance component such as ethyl butyrate to be dosed on carbon are placed in a glass jar (125 mL or 250 mL), the jar is tightly capped, and the sorbent is allowed to equilibrate with vapor of the fragrance component for several days. A 2:1 v/v solution of the fragrance component to be dosed in a solvent with a low boiling point (e.g., methanol or hexane) is added to activated carbon in granular form spread on a watch glass or beaker, so as to cover the sorbent, the container is placed in a fume hood, and the solution is allowed to evaporate. Next, a solution of the fragrance component and a solvent with a low boiling point is added to activated carbon heated to 103° C. while still hot. The resulting suspension is heated again to a temperature just above the boiling point of the solvent (the boiling points of methanol and hexane are 64.7 and 69° C. respectively) in order to volatize any remaining solvent, and then allowed to cool to room temperature. The resulting suspension, which is in liquid form, is added to activated carbon which has been heated to 103° C. and the treated activated carbon is then allowed to cool to room temperature. The fragrance-dosed activated carbon so prepared may be used for odor control applications as described earlier.

Example 6

Another modification of the same two-step and/or multi-step process as for Example 4 is RGC activated carbon granule 80×325 mesh size from Westvaco Corporation of Charleston, S.C. U.S.A. is continuously impregnated with two or more fragrances in successive continuous steps using a series of Shugi mixers, as described in Example 2.

Example 7

An article that incorporates the composition of the present invention is detailed below. A sorbent impregnated with fragrance from any of the previously-described process examples that is contained within an air-permeable "chamber" or container. The chamber may be comprised of paper, paperboard, wood, woven materials including cotton and polyester, nonwoven materials including films and laminates, ceramics including clays and porcelain, glass, metals including aluminum, steel, tin and bronze, or any combination thereof, wherein the chamber materials may or may not be coated to provide a moisture barrier to the contents. For instance, the volatile substance-controlling composition from any of the above examples is placed within a bag comprised of an air-permeable nonwoven polyethylene bag that is further contained within a supporting box structure wherein the bottom, top and edges are paperboard and at least two opposing sides and up to all four sides of the box are punctured or otherwise formed with numerous holes to permit free air circulation throughout the box and contents therein. Such a device can be used as a passive room or transport vehicle deodorizer.

Example 8

An absorbent article that includes the composition of the present invention is described below. An absorbent article as detailed in any one of U.S. Pat. Nos. 5,556,394, 5,554,145, 5,554,144, 5,554,143, 5,554,142, 5,643,588, 5,624,426, 5,609,587, 5,607,760, 5,575,784, 5,558,661, 5,997,521, 5,968,025, 5,906,603, 5,957,906, 6,118,041, and 6,107,537 is constructed. In this instance, however, a nonwoven substrate is impregnated with the composition of any of Examples 1-6 and allowed to dry. This substrate is cut to fit between the absorbent core and backsheet of the absorbent article and is so placed and the portions of the article are bonded to one another.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of controlling the spread of volatile substances, the method comprising the steps of:
   a) impregnating a fragrance component comprising at least one PRM onto a plurality of surfaces of a sorbent to form a volatile substance-controlling composition; and
   b) disposing the volatile substance-controlling composition into an article wherein the fragrance component is released from the sorbent primarily in the presence of one or more volatile substances when the volatile substances are adsorbed by the sorbent.

2. The method of claim 1, wherein the sorbent is selected from the group consisting of activated carbon, activated alumina, amorphous silica, crystalline silica, zeolite, ion exchange resin, metal bicarbonate, carbonate, cyclodextrin, metal oxide, crosslinked polyacrylate, and combinations thereof.

3. The method of claim 1, wherein the PRM is selected from the group consisting of linear aliphatic, branched aliphatic, aromatic, polyaromatic, and heterocyclic organic compounds having at least one of the following functional groups: carboxylic acid, alcohol, aldehyde, amine, chylene, ester or ketone.

4. The method of claim 1, wherein the article is a product selected from the group consisting of diapers, training pants, incontinence products, sanitary napkins, pantiliners, filters, room deodorizers, cleaning pads, dust cloths, clothes dryer aids and combinations thereof.

5. The method of claim 4, wherein the volatile substance-controlling composition is adjacent to a substrate component of the article and wherein the substrate component is selected from the group consisting of topsheets, backsheets, absorbent cores, waistbands, leg cuffs, side panels, and combinations thereof.

6. The method of claim 1, further comprising the step of combining the sorbent and the fragrance component in a mixing chamber wherein the fragrance component is added under at least 2 psi pressure higher than exists outside the mixing chamber.

7. The method of claim 6, wherein the fragrance component is added to the mixing chamber in the presence of an alcohol having no more than three carbons per molecule.

8. The method of claim 6, wherein the fragrance component is added in an amount of from about 10 to about 30 wt %, by weight of the composition.

* * * * *

UNITED STATES PATENT AND TRADEMARK OFFICE
CERTIFICATE OF CORRECTION

PATENT NO. : 7,549,598 B2
APPLICATION NO. : 11/803603
DATED : June 23, 2009
INVENTOR(S) : Bruce E. Tepper et al.

Page 1 of 1

It is certified that error appears in the above-identified patent and that said Letters Patent is hereby corrected as shown below:

Column 5

Line 63, delete "isobomyl" and insert --isobornyl--.

Column 6

Line 1, delete "isobomyl" and insert --isobornyl--.

Line 2, delete "cormbinations" and insert --combinations--.

Line 5, delete "isobomyl" and insert --isobornyl--.

Signed and Sealed this

Fifteenth Day of December, 2009

David J. Kappos
*Director of the United States Patent and Trademark Office*